United States Patent [19]

Mazess

[11] Patent Number: 5,218,963
[45] Date of Patent: Jun. 15, 1993

[54] ULTRASONIC BONE ANALYSIS DEVICE AND METHOD

[75] Inventor: Richard B. Mazess, Madison, Wis.

[73] Assignee: Lunar Corporation, Madison, Wis.

[21] Appl. No.: 775,876

[22] Filed: Oct. 15, 1991

[51] Int. Cl.$^5$ .............................................. A61B 8/00
[52] U.S. Cl. ........................... 128/661.03; 128/660.06
[58] Field of Search ...................... 128/660.01, 660.02, 128/661.03; 73/597, 599, 602

[56] References Cited

U.S. PATENT DOCUMENTS

| | | |
|---|---|---|
| 2,439,130 | 4/1948 | Firestone . |
| 3,345,863 | 10/1967 | Henry et al. . |
| 3,477,422 | 11/1969 | Jurist, Jr. et al. . |
| 3,587,561 | 6/1971 | Ziedonis . |
| 3,648,685 | 3/1972 | Hepp et al. . |
| 3,664,180 | 5/1972 | McDonald et al. . |
| 3,713,329 | 1/1973 | Munger . |
| 3,782,177 | 1/1974 | Hoop . |
| 3,847,141 | 11/1974 | Hoop . |
| 4,048,986 | 9/1977 | Ott . |
| 4,056,970 | 11/1977 | Sollish . |
| 4,105,018 | 8/1978 | Greenleaf et al. . |
| 4,138,999 | 2/1979 | Eckhart et al. . |
| 4,217,912 | 8/1980 | Hubmann et al. . |
| 4,233,845 | 11/1980 | Pratt, Jr. . |
| 4,235,243 | 11/1980 | Saha . |
| 4,250,895 | 2/1981 | Lees . |
| 4,316,183 | 2/1982 | Palmer et al. . |
| 4,361,154 | 11/1982 | Pratt, Jr. . |
| 4,421,119 | 12/1983 | Pratt, Jr. . |
| 4,476,873 | 10/1984 | Sorenson et al. . |
| 4,522,068 | 6/1985 | Smith . |
| 4,530,360 | 7/1985 | Duarte . |
| 4,597,292 | 7/1985 | Fujuii et al. . |
| 4,669,482 | 6/1987 | Ophir . |
| 4,774,959 | 10/1988 | Palmer . |
| 4,913,157 | 4/1990 | Pratt, Jr. et al. ............ 128/661.03 |
| 4,930,511 | 6/1990 | Rossman et al. ............ 128/661.03 |
| 4,941,474 | 7/1990 | Pratt, Jr. ...................... 128/660.01 |
| 5,042,489 | 8/1991 | Wiener et al. ................ 128/661.03 |
| 5,054,490 | 10/1991 | Rossman et al. ............ 128/661.03 |
| 5,143,069 | 9/1992 | Kwon et al. .................. 128/660.01 |

FOREIGN PATENT DOCUMENTS

| | | |
|---|---|---|
| 2318420 | 2/1977 | France . |
| WO87/07494 | 12/1987 | PCT Int'l Appl. . |
| 123748 | 3/1959 | U.S.S.R. . |
| 219853 | 6/1968 | U.S.S.R. . |
| 0341969 | 11/1989 | World Int. Prop. O. . |

OTHER PUBLICATIONS

Abenschein, W. and G. W. Hyatt, "Ultrasonics and Selected Physical Properties of Bone", *Clinical Orthopedics and Related Research*, No. 69, pp. 294–301 (1970).

Brown, S. A. and M. B. Mayor, "Ultrasonic Assessment of Early Callus Formation", *Biomedical Engineering*, vol. 11, No. 4, (Apr. 1976), pp. 124–128.

Brown, S. A. and M. B. Mayor, "Ultrasonic Prediction of Delayed or Nonunion of Fractures", *Proceedings of the Fifth New England Bioengineering Conference* (Apr. 15, 1977), pp. 229–233.

Craven, J. D. et al., "Measurement of the Velocity of Ultrasound in Human Cortical Bone and its Potential Clinical Importance", *Investigative Radiology*, vol. 8, pp. 72–77 (1973).

Gerlanc, M. et al., "Ultrasonic Study of Normal and Fractured Bone", *Clinical Orthopedics and Related Research*, pp. 175–180 (1975).

(List continued on next page.)

*Primary Examiner*—Francis Jaworski
*Attorney, Agent, or Firm*—Quarles & Brady

[57] ABSTRACT

An instrument for measuring the strength and integrity of bone in vivo by ultrasound pulse taking its data by measurement of the os calcis or heel bone. The measured data is processed so that the instrument is capable of presenting its output in units of estimated spinal bone density, a value of recognized clinical value and acceptance. It has been determined that, using both the changes in the speed of ultrasound in the patient's heel and the broadband ultrasonic attenuation of the ultrasonic pulse as it transmits through the patient, that a value for estimated spinal bone mineral density can be calculated which correlates very well with actual measured values of spine mineral density.

13 Claims, 2 Drawing Sheets

OTHER PUBLICATIONS

Greespan, M. and C. E. Tschiegg, "Sing-Around Ultrasonic Velocimeter for Liquids", *The Review of Scientific Instruments*, vol. 28, No. 11, pp. 897–901 (1957).

Hoop, J. M. and W. N. Clotfelter, "Ultrasonic Bone Density Measurements", Marshall Space Flight Center, the Fall Conference of the American Society for Nondestructive Testing (1970).

Lang, S., "Ultrasonic Method for Measuring Elastic Coefficients of Bone and Results on Fresh and Dried Bovine Bones", *IEEE Transactions on Bio-Medical Engineering*, vol. BME-17, No. 2 (Apr. 1970), pp. 101–105.

Langton, C. M. et al., "The Measurement of Broadband Ultrasonic Attenuation in Cancellous Bone", *Eng. Med.*, vol. 13, pp. 89–91 (1984).

Lees, S. and C. Davidson, "The Role of Collagen in the Elastic Properties of Calcified Tissues", *C. Journal of Biomechanics*, vol. 10, No. 7 (1977), pp. 473–486.

Lees, S., "Sonic Properties of Mineralized Tissue", *Tissue Characterization with Ultrasound*, CRC Publication 2, pp. 207–226 (1986).

Martin, B. and R. Haynes, "The Investigation of Bone's Substructure Using Megahertz Sound and A Porous Model", *ASME Publication* (Dec. 3, 1970).

Martin, B. and R. R. Haynes, "The Relationship Between the Speed of Sound and Stiffness of Bone", Biomechanics Laboratories, West Virginia University (1970).

Mather, B. S., "Comparison of Two Formulae in Vivo Prediction of Strength of the Femur", *Aerospace Medicine*, vol. 38, No. 12 (Dec. 1967), pp. 1270–1272.

McDicken, W. N., *Diagnostic Ultrasonics, pp. 35–61 (1976)*.

Okumura, K. H., "Preventative Diagnosis of Breakdown", Massachusetts Institute of Technology (1978).

Rich, C. et al., "Sonic Measurement of Bone Mass", *Progress in Development of Methods of Bone Densitometry*, pp. 137–146, (NASA 1966).

Rossman, P. J., "Measurements of Ultrasonic Velocity and Attenuation in the Human OS Calcis and Their Relationship Photon Absorptiometry Bone Mineral Measurements", Master's Thesis, University of Wisconsin-Madison, 1987.

Van Venrooij, G., "Measurement of Ultrasound Velocity in Human Tissue", *Ultrasonics*, Oct. (1971), pp. 240–242.

Wells, P. N. T., "Physical Principals of Ultrasonic Diagnosis", *Academic Press*, London (1969), pp. 1–27.

Yamada, H., "Strength of Biological Materials", pp. 53–57 (1970).

ULTRASONIC BONE ANALYSIS DEVICE AND METHOD

FIELD OF THE INVENTION

The present invention relates to the analysis of the strength and integrity of bone in vivo in a patient and relates, in particular, to the techniques for the use of ultrasound as a diagnostic technique to evaluate the strength and integrity of bones in vivo in patients.

BACKGROUND OF THE INVENTION

Several devices are presently marketed for measuring the physical properties and integrity of a member, such as a bone non-invasively, in vivo in a patient. Such non-invasive density measuring devices, or densitometers, are typically used to determine cumulative internal damage caused by micro-crushing and micro-fracturing of bone which occurs naturally in humans or animals over time. Such non-invasive density measuring instruments are also used to diagnose the existence and extent of osteoporosis, or loss of bone mineralization, a common chronic problem in elderly humans. The detection, cure and prevention of osteoporosis are currently areas of intense medical interest, particularly in the United States, as a greater number of patients are developing complications resulting from cumulative trabecular bone loss.

One current methodology employed by bone densitometry instruments is based on dual photon energy beams passed through a patient. The sum of the energies passed through the patient at a series of data points are captured by the instrument and, after proper mathematical analysis, are analyzed to locate the bones within the body and to calculate the density of those bones. This technique is sometimes referred to as dual-photon absorptiometry. The commercial current models utilizing this technology are based on dual energy x-ray beams passed through the patient, and are therefore sometimes referred to as dual-energy x-ray apsortiometry, or DEXA instruments. Such instruments are typically used to analyze either the spine or the femur of the patient in whom it is desired to diagnose whether or not osteoporosis might be present. Using such instruments, the average spine bone mineral density (referred to below as "BMD") for elderly normal (non-osteoporotic) subjects without fracture is about 1.0 grams per square centimeter. This value is often considered a threshold for spine fracture, and patients with a bone mineral density value below that 1.0 threshold value are often defined to be osteoporotic or at high risk of fracture. Since bones in a body vary in their extent of mineral density, the threshold of clinical significance must accordingly vary depending on the bone specified.

Various instruments have also been previously proposed to measure such bone density non-invasively using ultrasonic, rather than x-ray measurement techniques. One such ultrasonic densitometer is described in U.S. Pat. No. 4,930,511. In that patent, it is specifically described that the transit time of an ultrasonic pulse transmitted through a living member is related to the bone mineral density of the member. It is further described that the broadband attenuation of the ultrasonic pulse through the member may also be utilized as a measure of mineral density of the bone in vivo. Alternatively, it is described that an ultrasound instrument may calculate both the transit time of the acoustic pulse and the broadband ultrasonic attenuation of the acoustic pulse and may use both results to determine the density of the bone member. The particular instrument described in that patent was constructed to calculate and display a mathematical comparison between measured transit time and normal transit time, or measured attenuation and normal attenuation, as an indication of the density of the member. It is these mathematical comparisons which are presented to the clinical user on the display device described in that instrument.

SUMMARY OF THE INVENTION

The present invention is summarized in that an ultrasonic densitometer for measuring the physical properties and integrity of a member in vivo includes a pair of spaced ultrasonic transducers between which the heel of a patient may be placed and means to transmit an ultrasonic pulse from one transducer to the other through the member. The instrument then calculates both the velocity of the ultrasonic pulse through the member and the broadband ultrasonic attenuation of the pulse as it passes through the member, and, from these two numbers, calculates an estimated spinal bone mineral density, which is displayed on the output of the instrument, so as to provide a numerical indication to the clinician which is both predictive of bone mineral density in the spine and similar to the range and values of numbers which the clinician has come to expect from current bone densitometers.

It is an object of the present invention to provide a more accurate way for performing bone mineral density analysis by ultrasound, by combining different types of ultrasonic analysis to obtain maximum reproducibility and consistency.

It is another object of the present invention to provide an ultrasonic bone mineral density analysis instrument which presents its output to the clinician by presenting numerical values in the same range as analogous values determined by DPX and other dual energy photon instruments, to facilitate clinical use and analysis of data on bone mineral density measured by the instrument.

Other objects, advantages, and features of the present invention will become apparent from the following specification when taken in conjunction with the accompanying drawings.

DETAILED DESCRIPTION OF THE INVENTION

The present invention requires an apparatus which is capable, under software control, of measuring both the speed of sound and the attenuation of an ultrasonic pulse transmitted between two transducers, in between which a portion of the patient's body is placed. While the invention is directed in particular toward a methodology for calculating and expressing numerical results from the data recovered, it is useful to understand generally how such an apparatus may operate to recover its raw data in order that the manipulation and analysis of the data may be properly understood. Therefore an illustrative apparatus is described first.

Figure 1:
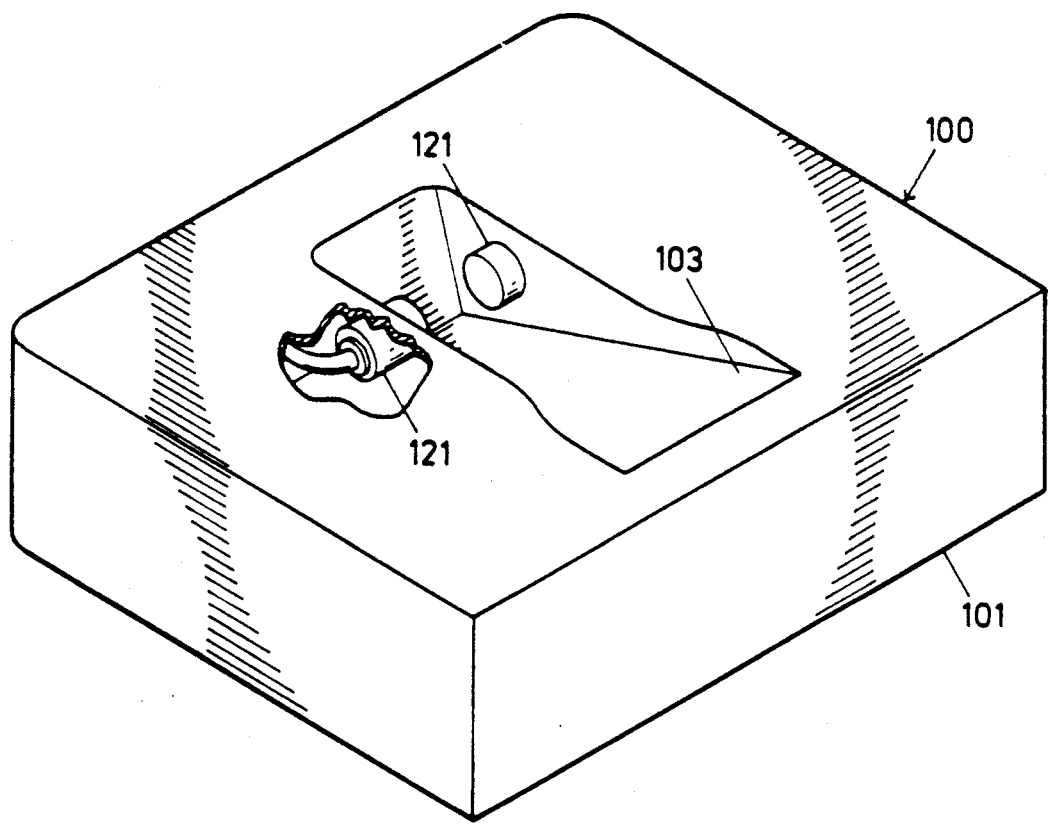
FIG. 1 is a perspective view of an embodiment of an ultrasound densitometer device constructed in accordance with the present invention.

Shown in FIG. 1, and generally illustrated at 100, is an ultrasonic densitometer within which the present invention may be implemented. The densitometer 100 includes a largely rectangular housing 101 within which is formed a basin 103. The basin 103 is intended to be filled with a liquid standard homogenous reference material, such as water. The apparatus may include temperature regulation mechanism to ensure that the water in the basin 103 is held steady at a constant temperature. Located in the sides of the basin 103 are a pair of ultrasonic transducers 121. Either of the transducers 121 is capable of transmitting, or detecting, the transmission of an ultrasonic signal. The transducers 121 may be single element transducers, or may also include an array of transducers, of the type described in some detail in the specification of U.S. Pat. No. 5,042,489. Many of the details of how such transducers, and particularly an array of transducers, may be energized are described in said U.S. Pat. No. 5,042,489. The specification of which is hereby incorporated by reference.

Figure 2:
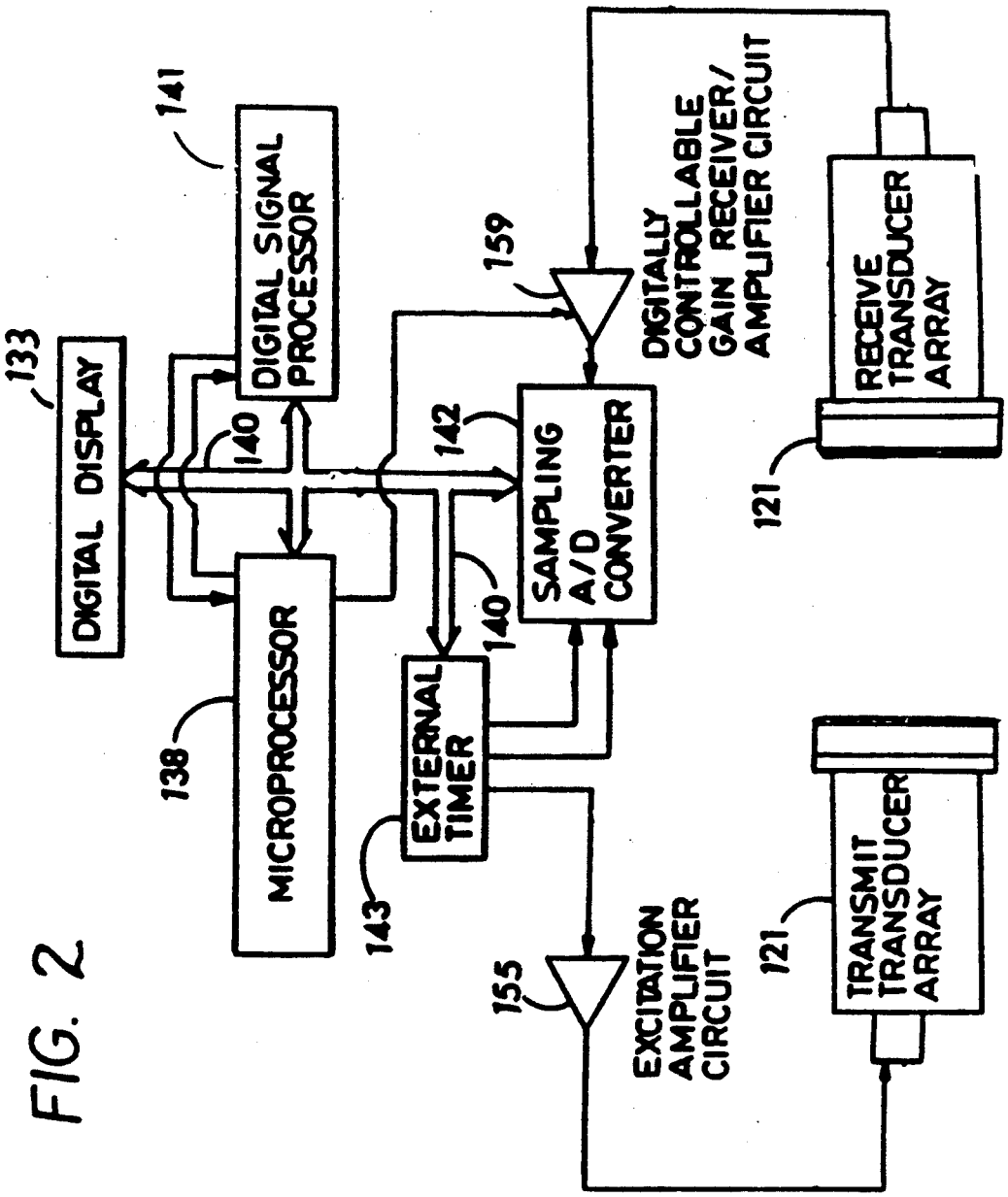
FIG. 2 is a schematic block diagram view of the circuitry of the ultrasound densitometry device constructed in accordance with the present invention.

Shown in FIG. 2 is a simplified schematic illustrating the minimal digital electronics necessary to operate an apparatus such as illustrated in FIG. 1. The apparatus is operated under the control of a microprocessor 138 which is connected to control the operation of a timer 143. The timer 143 is capable of inducing an excitation pulse from an excitation amplifier circuit 155 connected to drive one of the transducers 121, designated the transmit transducer. The other transducer, designated a receive transducer 121, has its output connected to a digitally controllable gain amplifier circuit 159 which has its output connected, in turn, to a sampling analog-to-digital (A to D) converter 142. The A to D converter 142 has its output connected to a data bus 140 which is also connected to the microprocessor 138. A digital signal processing circuit 141 is connected to the data bus 140, as is a digital display 143.

In its operation, the microprocessor 138 initiates operation of, and generally controls the mode of operation, of the remaining elements of the circuitry of FIG. 2. When an ultrasonic pulse is to be initiated, the microprocessor 138 coordinates with the timer 143 to initiate an excitation pulse circuit from excitation amplifier 155. This causes an ultrasonic pulse to be transmitted from the transmit transducer 121. The pulse travels through the water, and through the heel of the patient which has been placed between the transducers 121 in the basin 103. The receive transducer 121 receives the ultrasonic signal in the form that it has been transmitted through the heel of the patient. The output signal is transmitted through the gain controllable amplifier circuit 159 to the A to D converter 142. The sampling A to D converter 142 is capable of converting the analog output received into a digital format, so that it can be processed by the microprocessor 138 under software control. The dedicated digital signal processor circuit 141 is to facilitate the signal processing of the received data from the A to D converter, and may include appropriate discrete Fourier transform circuitry of the type well known to those of ordinary skill in the art. The output from the microprocessor can be displayed on the digital display 143. Again, while this discussion is intended to illustrate generally the functioning of these components of an illustrative instrument, the function of these and similar components is described in more detail in the above mentioned U.S. Pat. No. 5,042,489, to which reference may be had as appropriate.

This instrument is capable of measuring both the speed of sound and/or velocity of the ultrasonic pulse as it passes through the member and also the attenuation of the pulse, preferably the broadband ultrasonic attenuation. The speed of sound may simply be measured by measuring the time it takes for the ultrasonic pulse to transit from the transmit transducer to the receive transducer. Since the distance between the transducers is fixed, the distance can be stored in memory and the speed of propagation of the ultrasonic pulse through the member can readily be mathematically calculated, without undue difficulty, by dividing the distance by the time. The ultrasonic attenuation is a diminution of the ultrasonic wave form due to the propagation of the wave form through the subject, or through a standard. It has been previously recognized that there is a linear relationship between the ultrasonic attenuation, measured in decibels, at specific frequencies, and changes in those frequencies. The slope of that relationship, expressed in dB/MHz, is a linear relationship which we refer to as the broadband ultrasonic attenuation (or BUA). the broadband ultrasonic attenuation is dependent upon the physical properties and integrity of the substance being tested. Previous research has demonstrated a co-relation between the BUA and the bone mineral density of the os calcis of the human heel. Thus BUA may be used to evaluate the mineral content and integrity of the bones of the patient.

In an instrument of this type, the speed and/or velocity of sound and the attenuation may be measured simultaneously or sequentially. Repetitive ultrasonic pulses may be launched, measured and averaged to reduce the noise contribution to the output values. While BUA is the preferred measurement of attenuation, other techniques of attenuation measurement, such as successive narrow band attenuation analysis or use of an input waveform which varies over a frequency range, may also be used.

In any instrument intended to provide a diagnostic of medical condition in a patient, the reliability and reproducibility of the measurement are critical attributes. In general, it has been found that there does exist a correlation between measured speed of sound through the os calcis and the measured bone mineral density BMD of a spine or femur of a patient, as determined by more traditional densitometry techniques, such dual-energy x-ray absorptiometry instruments or DEXA. It has also been found that there exists a correlation between BUA as determined through the os calcis and measurement of spinal or femural bone mineral density as determined by DEXA analysis of the patient's spine or femur. What has been found here, surprisingly, is that the combination of both speed of sound and broadband attenuation data measured in the same patient can be combined to give an output indicative of bone mineral density of the spine which is more reliable, and more accurate, than could be obtained from the use of either of these measurements alone. Accordingly, using both these measurements, in combination, in an ultrasonic densitometry instrument, it is possible to present to the clinician a numerical output value on a digital display connected to the device in units normally associated with bone mineral density of the spine. In other words, the output of the device instead of being in units of speed of sound, or units of BUA, is presented in units of spinal bone mineral density (BMD). Using this approach, the instrument is capable of providing a numerical output on a value scale recognized and accepted by clinicians and with an accuracy, a reliability, and a reproducibility, not heretofore achievable with ultrasonic approaches to bone densitometry.

One other concept may be usefully derived utilizing this same approach. In addition to calculating the estimated bone mineral density of the spine, it is also desirable to present outputs from the instrument which are expressed as differents relative to an idealized young, normal, patient. In other words, an idealized standard (a young, "normal," patient of a given sex and age range) is created having a pre-selected value for bone mineral density. Then the output of the instrument can be presented as a percentage related to the average young, normal value. Percentages which are less than 100 would correspond to bone mineral densities which bear some fractional proportion to the idealized young, normal average. Values which are over 100 would indicate bone mineral densities proportionately higher than the defined average for young, normal, individuals. In this fashion, another readily understandable numerical value is presented to the clinician, who does not then need to know or appreciate the absolute BMD values.

In order that the manipulation of this data and the value of the calculated result be properly understood, four tables of actual patient data are set forth in Tables 1 through 4 below. In each table, the initials of the patient are given in the left-hand margin, followed by the patient's age. Following on the table are the broadband ultrasonic attenuation (BUA) and the speed of sound (SOS) measured to the patient, scaled as described below. Following that, the BUA and the SOS of the patient are given as percentages of young, normal, followed by an average calculated from the BUA and SOS values taken together. Following that, on each table are estimated, or calculated, values of spinal BMD. The estimated BMD values are calculated using BUA, and using SOS, and then combined estimated values are calculated for each patient as the average of estimate spinal BMD values created by BUA and SOS. The calculation of these values will be described further below. Also presented on each table is the measured spinal and femural BMD, as determined by actual DEXA analysis of the spine and the femur of the same patients.

TABLE 1

|  | AGE | SCALED BUA | SCALED SOS | % YOUNG NORMAL BUA | % YOUNG NORMAL SOS | % YOUNG NORMAL AVG | SPINE ESTIMATE BUA | SPINE ESTIMATE SOS | SPINE ESTIMATE AVG | BMD SPINE | BMD FEMUR |
|---|---|---|---|---|---|---|---|---|---|---|---|
| MV | 84 | 91 | 62 | 55 | 34 | 44 | 0.727 | 0.574 | 0.651 | 0.497 | 0.549 |
| EG | 68 | 92 | 89 | 56 | 49 | 53 | 0.737 | 0.707 | 0.722 | 0.551 | 0.509 |
| BM | 68 | 84 | 47 | 46 | 26 | 36 | 0.651 | 0.500 | 0.576 | 0.594 | 0.613 |
| EV | 71 | 100 | 123 | 66 | 68 | 67 | 0.830 | 0.871 | 0.851 | 0.600 | 0.595 |
| LC | 73 | 91 | 88 | 55 | 49 | 52 | 0.732 | 0.703 | 0.717 | 0.630 | 0.702 |
| WW | 72 | 95 | 112 | 60 | 62 | 61 | 0.772 | 0.818 | 0.795 | 0.634 | 0.608 |
| AV | 66 | 97 | 123 | 62 | 68 | 65 | 0.795 | 0.871 | 0.833 | 0.683 | 0.585 |
| VS | 67 | 86 | 109 | 48 | 61 | 54 | 0.670 | 0.805 | 0.738 | 0.689 | 0.713 |
| MB | 83 | 91 | 103 | 55 | 57 | 56 | 0.730 | 0.772 | 0.751 | 0.699 | 0.722 |
| HB | 62 | 94 | 109 | 58 | 60 | 59 | 0.760 | 0.803 | 0.781 | 0.730 | 0.554 |
| SN | 55 | 93 | 89 | 57 | 49 | 53 | 0.748 | 0.708 | 0.728 | 0.731 | 0.628 |
| LB | 75 | 93 | 119 | 57 | 66 | 62 | 0.752 | 0.854 | 0.803 | 0.737 | 0.658 |
| MB | 69 | 103 | 102 | 70 | 57 | 64 | 0.867 | 0.770 | 0.819 | 0.739 | 0.757 |
| MG | 61 | 103 | 128 | 71 | 71 | 71 | 0.875 | 0.897 | 0.886 | 0.742 | 0.606 |
| WK | 67 | 97 | 107 | 63 | 59 | 61 | 0.805 | 0.796 | 0.801 | 0.744 | 0.549 |
| JT | 62 | 116 | 149 | 89 | 83 | 86 | 1.028 | 0.999 | 1.013 | 0.747 | 0.726 |
| GH | 52 | 106 | 108 | 75 | 60 | 68 | 0.910 | 0.801 | 0.855 | 0.752 | 0.562 |
| GK | 65 | 113 | 134 | 84 | 74 | 79 | 0.987 | 0.926 | 0.956 | 0.758 | 0.648 |
| JW | 64 | 93 | 82 | 58 | 45 | 51 | 0.756 | 0.670 | 0.713 | 0.761 | 0.635 |
| RT | 58 | 107 | 129 | 76 | 72 | 74 | 0.918 | 0.902 | 0.910 | 0.785 | 0.777 |
| GW | 77 | 101 | 117 | 69 | 65 | 67 | 0.852 | 0.841 | 0.847 | 0.786 | 0.670 |
| HW | 62 | 89 | 96 | 52 | 53 | 52 | 0.701 | 0.741 | 0.721 | 0.797 | 0.662 |
| JJ | 56 | 85 | 107 | 47 | 59 | 53 | 0.662 | 0.793 | 0.728 | 0.806 |  |
| AN | 37 | 115 | 142 | 87 | 79 | 83 | 1.013 | 0.966 | 0.990 | 0.815 | 0.771 |
| RD | 78 | 94 | 131 | 59 | 72 | 66 | 0.766 | 0.909 | 0.837 | 0.826 | 0.654 |
| LS | 85 | 87 | 66 | 49 | 37 | 43 | 0.679 | 0.595 | 0.637 | 0.834 |  |
| LM | 49 | 103 | 108 | 71 | 60 | 65 | 0.868 | 0.797 | 0.833 | 0.841 | 0.589 |
| BR | 51 | 118 | 174 | 91 | 97 | 94 | 1.050 | 1.122 | 1.086 | 0.856 | 0.691 |
| DB | 59 | 92 | 130 | 56 | 72 | 64 | 0.738 | 0.905 | 0.821 | 0.864 |  |
| BR | 76 | 97 | 118 | 63 | 65 | 64 | 0.800 | 0.846 | 0.823 | 0.896 | 0.631 |
| HV | 59 | 107 | 122 | 76 | 68 | 72 | 0.913 | 0.869 | 0.891 | 0.898 | 0.709 |
| MW | 58 | 96 | 122 | 61 | 68 | 64 | 0.787 | 0.867 | 0.827 | 0.899 | 0.664 |
| MF | 61 | 113 | 135 | 84 | 75 | 79 | 0.984 | 0.932 | 0.958 | 0.909 | 0.683 |
| GB | 64 | 104 | 128 | 72 | 71 | 72 | 0.883 | 0.897 | 0.890 | 0.919 | 0.782 |
| DH | 58 | 111 | 153 | 81 | 85 | 83 | 0.960 | 1.018 | 0.989 | 0.919 | 0.739 |
| DA | 40 | 115 | 176 | 87 | 98 | 92 | 1.011 | 1.130 | 1.071 | 0.931 | 0.750 |
| MH | 61 | 119 | 166 | 93 | 92 | 92 | 1.063 | 1.080 | 1.071 | 0.931 | 0.764 |
| GM | 49 | 110 | 142 | 80 | 79 | 79 | 0.953 | 0.964 | 0.959 | 0.958 | 0.843 |
| TA | 54 | 110 | 156 | 80 | 86 | 83 | 0.952 | 1.031 | 0.991 | 0.967 |  |
| SB | 62 | 112 | 146 | 83 | 81 | 82 | 0.974 | 0.985 | 0.979 | 0.991 |  |
| CE | 76 | 103 | 135 | 70 | 75 | 73 | 0.867 | 0.933 | 0.900 | 1.068 | 0.652 |

TABLE 2

| | AGE | BUA | SCALED SOS | % YOUNG NORMAL | | | SPINE ESTIMATE | | | BMD | |
|---|---|---|---|---|---|---|---|---|---|---|---|
| | | | | BUA | SOS | AVG | BUA | SOS | AVG | SPINE | FEMUR |
| MF | 21 | 133 | 190 | 110 | 105 | 108 | 1.219 | 1.199 | 1.209 | 1.007 | 0.917 |
| BR | 37 | 120 | 148 | 94 | 82 | 88 | 1.072 | 0.992 | 1.032 | 1.026 | 0.836 |
| KA | 44 | 131 | 175 | 109 | 97 | 103 | 1.203 | 1.128 | 1.165 | 1.046 | |
| CO | 21 | 109 | 179 | 79 | 99 | 89 | 0.939 | 1.145 | 1.042 | 1.096 | 0.997 |
| PD | 23 | 118 | 178 | 90 | 99 | 94 | 1.041 | 1.141 | 1.091 | 1.102 | 0.798 |
| MM | 47 | 130 | 191 | 107 | 106 | 107 | 1.191 | 1.203 | 1.197 | 1.126 | 0.75 |
| BM | 28 | 125 | 194 | 100 | 108 | 104 | 1.127 | 1.218 | 1.173 | 1.148 | 1.043 |
| PG | 37 | 106 | 186 | 75 | 103 | 89 | 0.909 | 1.180 | 1.044 | 1.163 | |
| CS | 45 | 117 | 176 | 90 | 98 | 94 | 1.037 | 1.132 | 1.084 | 1.176 | 1.054 |
| PU | 42 | 110 | 140 | 81 | 77 | 79 | 0.957 | 0.953 | 0.955 | 1.182 | 1.030 |
| SS | 27 | 110 | 150 | 80 | 83 | 82 | 0.953 | 1.002 | 0.977 | 1.185 | 0.952 |
| CK | 34 | 127 | 206 | 103 | 114 | 109 | 1.156 | 1.276 | 1.216 | 1.211 | 0.934 |
| MH | 46 | 131 | 181 | 108 | 100 | 104 | 1.200 | 1.154 | 1.177 | 1.226 | 0.952 |
| LA | 33 | 128 | 172 | 104 | 95 | 99 | 1.160 | 1.110 | 1.135 | 1.252 | 0.975 |
| VC | 27 | 122 | 173 | 97 | 96 | 96 | 1.098 | 1.118 | 1.108 | 1.279 | 0.877 |
| MB | 36 | 121 | 210 | 94 | 116 | 105 | 1.077 | 1.294 | 1.185 | 1.299 | 0.792 |
| KS | 49 | 130 | 142 | 107 | 79 | 93 | 1.185 | 0.964 | 1.074 | 1.316 | 1.001 |
| DS | 49 | 137 | 185 | 116 | 103 | 109 | 1.271 | 1.174 | 1.222 | 1.368 | 0.863 |
| SM | 36 | 142 | 186 | 123 | 103 | 113 | 1.329 | 1.181 | 1.255 | 1.377 | 1.074 |
| DC | 37 | 150 | 228 | 134 | 127 | 130 | 1.426 | 1.384 | 1.405 | 1.380 | 1.169 |

TABLE 3

| | AGE | BUA | SCALED SOS | % YOUNG NORMAL | | | SPINE ESTIMATE | | | BMD | |
|---|---|---|---|---|---|---|---|---|---|---|---|
| | | | | BUA | SOS | AVG | BUA | SOS | AVG | SPINE | FEMUR |
| AC | 59 | 116 | 136 | 88 | 75 | 82 | 1.023 | 0.933 | 0.978 | 1.05 | 0.781 |
| BB | 50 | 104 | 128 | 72 | 71 | 72 | 0.885 | 0.899 | 0.892 | 1.060 | 0.798 |
| CM | 61 | 103 | 108 | 71 | 60 | 65 | 0.873 | 0.797 | 0.835 | 1.061 | 0.904 |
| NW | 63 | 142 | 198 | 123 | 110 | 116 | 1.329 | 1.237 | 1.283 | 1.109 | 0.967 |
| RH | 55 | 133 | 197 | 111 | 109 | 110 | 1.221 | 1.234 | 1.228 | 1.122 | 0.808 |
| CL | 62 | 126 | 191 | 102 | 106 | 104 | 1.142 | 1.201 | 1.171 | 1.235 | 1.001 |
| SW | 56 | 114 | 173 | 86 | 96 | 91 | 1.001 | 1.117 | 1.059 | 1.238 | 0.881 |
| DM | 51 | 114 | 192 | 86 | 106 | 96 | 1.003 | 1.208 | 1.105 | 1.253 | 0.856 |
| AL | 70 | 109 | 161 | 79 | 89 | 84 | 0.941 | 1.058 | 1.000 | 1.28 | 0.992 |
| MW | 69 | 125 | 142 | 101 | 78 | 90 | 1.133 | 0.963 | 1.048 | 1.280 | 0.920 |
| IP | 67 | 129 | 201 | 105 | 112 | 108 | 1.174 | 1.253 | 1.213 | 1.331 | 0.975 |

TABLE 4

| | AGE | BUA | SCALED SOS | % YOUNG NORMAL | | | SPINE ESTIMATE | | | BMD | |
|---|---|---|---|---|---|---|---|---|---|---|---|
| | | | | BUA | SOS | AVG | BUA | SOS | AVG | SPINE | FEMUR |
| HB | 44 | 118 | 147 | 90 | 81 | 86 | 1.043 | 0.988 | 1.016 | 1.000 | 0.852 |
| JB | 34 | 122 | 175 | 96 | 97 | 97 | 1.093 | 1.127 | 1.110 | 1.161 | 1.041 |
| RM | 30 | 130 | 192 | 107 | 106 | 107 | 1.187 | 1.206 | 1.197 | 1.187 | |
| JE | 35 | 138 | 166 | 117 | 92 | 105 | 1.279 | 1.083 | 1.181 | 1.197 | 0.985 |
| JL | 34 | 131 | 193 | 108 | 107 | 108 | 1.199 | 1.215 | 1.207 | 1.266 | 1.180 |
| JT | 32 | 142 | 195 | 123 | 108 | 115 | 1.326 | 1.222 | 1.274 | 1.299 | 1.087 |
| DS | 27 | 128 | 223 | 104 | 123 | 114 | 1.167 | 1.357 | 1.262 | 1.312 | 1.089 |
| DS | 33 | 134 | 212 | 113 | 118 | 115 | 1.238 | 1.307 | 1.272 | 1.312 | 1.089 |
| SW | 34 | 134 | 230 | 112 | 128 | 120 | 1.233 | 1.395 | 1.314 | 1.420 | |

The data presented in these tables was created from measurements on actual patients taken using the instrument of FIGS. 1 and 2. Table 1 illustrates values obtained, and the results calculated, for patients who were diagnosed as osteoporotics. All the osteoporotic patients were over the age of 50 and female. Table 2 illustrates values measured on female, young normals who were diagnosed not to be osteoporotic and who were under the age of 50. Table 3 illustrates values obtained and estimates calculated from measurements on females above the age of 50 who were determined not to be osteoporotic.

Table 4 illustrates values obtained and estimates calculated from measurements of young males (less than age 50) who were also not deemed to be osteoporotic.

In each of the above tables, data was calculated as follows: The BUA value was calculated as the measured slope of the linerationship between ultrasonic attenuation and frequency for the frequency spectrum of the received ultrasonic pulse. This value, expressed in dB/MHz, was not scaled as presented in these tables. A median BUA value for young, normal, adults would be 125. The speed of sound number, measured in meters per second, was scaled by subtraction of 1380 from the raw sound velocity number, to scale the SOS, or speed of sound number, as presented on Tables 1 through 4. The scaling is done so that the SOS numbers are in the same numerical range as the BUA numbers.

For the percentage of young normal values on the tables, a idealized patient was determined. The idealized young, normal, patient had a BUA of 125 dB/MHz. The average idealized young, normal value for SOS was 1560, giving a scaled value of 180. The percentage of young, normal values for BUA and for SOS was determined simply by taking the measured value of the BUA or SOS for that patient and dividing that by the defined value for the young, normal, and multiplying by 100, to derive a value expressed as a percentage of young normal. The two percentages, for percent of young normal for BUA, and percent of young normal for SOS, were then averaged together to obtain the average young normal value of each of the patients as presented in the seventh column on the tables.

On each of the Tables 1 through 4 there is also a column group labeled "Spine Estimate," with columns labelled "BUA," "SOS," and "Average." Each of these values represents a calculated, not measured, estimate of spine BMD mathematically generated from the BUA and scaled SOS data presented on the tables. A mathematical function was utilized to determine those values. The function is as follows: Estimated Spine Bone Mineral Density = $AX + B$ In the above formula, A and B represent constants and X represents the input value of either BUA or scaled SOS. The formula is a simple linear equation in which the A represents a constant value of the relationship between the variables and B represents a intercept of minimum spine bone mineral density. The value of the constant A was calculated so as to give, for each of BUA and SOS, a numerical value of calculated spine BMD which closely approximated the values achieved from DEXA spine bone mineral analysis, and which deviated from normal values with a standard deviation approximating that of measured spine bone mineral density from real patients. For the conversion from BUA to calculated spine BMD based on BUA, for the group of subjects in Table 1, for example, the constant A had a value of 0.360826 and the value constant B had a value of 0.616105. For the corresponding function between scaled SOS value and calculated spine bone mineral density based on SOS, the constant A had a value of 0.331029 and the value B had a value of 0.661585. It is these equations, with these or equivalent constants, which were used in the Tables 1 through 4 to calculate the "spine estimate" calculated values of spine BMD based on BUA and SOS. The "average" value was achieved by averaging the two estimated values for spinal or femural bone mineral density calculated using BUA and SOS.

In essence, it has been found that the use of both BUA and SOS in calculating estimated bone mineral density achieves a higher degree of precision and correlates better with actual measured spinal bone density than either BUA or SOS used alone. The above-identified values for calculated spine bone mineral density, based on BUA alone, when regressed on the actual values of measured DEXA spinal bone mineral density, achieved an R squared value of 0.6129. The comparable correlation between estimated spine BMD based on SOS and actual measured DEXA spine BMD is 0.6468. When both BUA and SOS are combined together to give the average estimated spine BMD value, the R squared value increases to 0.6761. This represents a correlation in excess of 0.8, and indicates a very high degree of correlation between calculated estimated bone mineral density based on ultrasound analysis of the os calcis and actual measured spinal BMD measured by the most accepted and utilized technology available for investigating this diagnostic parameter.

The reliability and reproducibility, and thus the clinical utility, of the estimated BMD values is an important asset of this method of providing output values from an ultrasonic instrument. Using this approach of calculating BUA, calculating scaled SOS, and estimating spinal BMD from the two values combined, a series of measurements were taken on real patients. Eighty-six scans were performed on sixteen separate subjects. The repetitive analysis data was then analyzed to determine the reliability, or precision, of the values measured. Precision, for these purposes, was defined as a percentage coefficient of variation, or mean standard deviation times 100. Thus, for precision analysis, the lower number indicates greater reproducibility and thus reliability of the parameter. From this set of data, the average precision for the BUA values was 2.02. For the values of scaled SOS, the average precision was 2.65. For a combined value of percent of young normal determined from both BUA and SOS, the average precision was 1.85. Finally, for estimated or calculated BMD, calculated from both BUA and SOS, the average precision was 1.44. Thus this combined output parameter not only is scaled such that the absolute values are better understood by clinicians, it is more reliable and reproducible than other output parameters from ultrasonic measurement of bone integrity. This precision enables clinicians to have a greater confidence in the output values and permits the more reliable tracking of BMD over time.

While it is preferred that the output of calculated BMD presented by the instrument, based on measured BUA and SOS, be scaled in terms of spinal BMD, it is also possible to express this output parameter in terms of BMD of another bone instead. For example, the output value could be expressed instead in terms of BMD of the femur or of the os calcis. If the calculated BMD were presented for another bone, the output values would have to be properly scaled to give values for that other member which relate to clinical experience for the other members.

It is to be understood that the present invention is not to be interpreted to be limited to the particular embodiment described here, but that instead it encompasses all variations thereon which come within the scope of the following claims.

I claim:

1. A method of analyzing and indicating the bone mineral content of a patient in vivo to a clinician comprising the steps of
   providing a pair of spaced apart ultrasonic transducers;
   placing the heel of the patient between the ultrasonic transducers;
   launching an ultrasonic pulse from one transducer toward the other through the heel of the patient;
   determining the speed of the ultrasonic pulse as it travels through the heel of the patient;
   determining the attenuation of the ultrasonic pulse as it travels through the heel of the patient;
   calculating a numerical estimated bone mineral density of the patient from the determined speed and determined attenuation of the ultrasonic pulse; and
   displaying to the clinician the calculated numerical value of estimated bone mineral density.

2. A method as claimed in claim 1 wherein the speed of the ultrasonic pulse is scaled before the estimated bone mineral density is calculated.

3. A method as claimed in claim 1 wherein the calculation of estimated bone mineral density is performed by multiplying each of the determined speed and the determined attenuation values by constants and adding other constants thereto to derive a value of estimated bone mineral density in units corresponding to grams per square centimeter of bone.

4. A method as claimed in claim 1 wherein the estimated bone mineral density is spinal bone mineral density.

5. A method as claimed in claim 1 wherein the estimated bone mineral density is femural bone mineral density.

6. A method of analyzing and indicating the mineral content of a patient in vivo to a clinician comprising the steps of
providing a pair of spaced apart ultrasonic transducers;
placing the heel of the patient between the ultrasonic transducers;
launching an ultrasonic pulse from one transducer toward the other through the heel of the patient;
determining the speed of the ultrasonic pulse as it travels through the heel of the patient;
determining the attenuation of the ultrasonic pulse as it travels through the heel of the patient;
calculating a percentage relationship between the measured value for speed of the ultrasonic pulse and a preselected standard value for a young, normal, individual;
calculating a percentage relationship between the measured value for attenuation of the ultrasonic pulse and a preselected standard value of attenuation for a young, normal, individual
averaging the calculated percentage relationship values; and
displaying to the clinician the average percentage relationship value.

7. A method of analyzing the mineral content of a bone, other than the os calcis, in the patient in vivo and indicating the result to a clinician comprising the steps of:
providing a pair of spaced apart ultrasonic transducers;
placing the heel of the patient between the ultrasonic transducers;
launching at least one ultrasonic pulse from one transducer toward the other through the heel of the patient; measuring the speed of an ultrasonic pulse as it travels through the heel of the patient;
measuring the attenuation of an ultrasonic pulse as it travels through the heel of the patient;
calculating an estimated value of bone mineral density for the bone by mathematically combining the measured speed of the ultrasonic pulse and a measured attenuation of the ultrasonic pulse; and
displaying to the clinician the average percentage relationship value.

8. A method as claimed in claim 7 wherein the bone is the spine.

9. A method as claimed in claim 7 wherein the bone is the femur.

10. A method as claimed in claim 7 wherein the determined ultrasonic attenuation is broadband ultrasonic attenuation.

11. A method as claimed in claim 7 wherein the calculation of estimated value of bone mineral density for the bone is performed by multiplying each of the measured speed and the measured attenuation values by constants and adding other constants thereto to derive a value of estimated bone mineral density in units corresponding to grams per square centimeter of bone.

12. A method of analyzing and indicating the bone mineral content of a patient in vivo to a clinician comprising the steps of:
providing a pair of spaced apart ultrasonic transducers;
placing the heel of the patient between the ultrasonic transducers;
launching an ultrasonic pulse from one transducer toward the other through the heel of the patient;
determining the speed of the ultrasonic pulse as it travels through the heel of the patient;
determining the attenuation of the ultrasonic pulse as it travels through the heel of the patient;
calculating a numerical estimated bone mineral density of the patient from the determined speed and determined attenuation of the ultrasonic pulse by multiplying each of the determined speed and the determined attenuation values by constants and adding other contents thereto to derive a value of estimated bone mineral density in units corresponding to grams per square centimeter of bone; and
displaying to the clinician the calculated numerical value of estimated bone mineral density.

13. A method of analyzing the mineral content of a bone, other than the os calcis, in the patient in vivo and indicating the result to a clinician comprising the steps of:
providing a pair of spaced apart ultrasonic transducers;
placing the heel of the patient between the ultrasonic transducers;
launching at least one ultrasonic pulse from one transducer toward the other through the heel of the patient;
measuring the speed of an ultrasonic pulse as it travels through the heel of the patient;
measuring the attenuation of an ultrasonic pulse as it travels through the heel of the patient;
calculating an estimated value of bone mineral density for the bone by multiplying each of the measured speed and the measured attenuation values by contents and adding other constants thereto to derive a value of estimated bone mineral density in units corresponding to grams per square centimeter of bone; and
displaying to the clinician the average percentage relationship value.

* * * * *